United States Patent
Li et al.

(10) Patent No.: US 12,343,203 B2
(45) Date of Patent: Jul. 1, 2025

(54) ULTRASOUND-BASED DEVICE LOCALIZATION

(71) Applicant: KONINKLIJKE PHILIPS N.V., Eindhoven (NL)

(72) Inventors: Sibo Li, Waltham, MA (US); Kunal Vaidya, Boston, MA (US); Molly Lara Flexman, Melrose, MA (US); Alyssa Torjesen, Charlestown, MA (US); Ameet Kumar Jain, Boston, MA (US); Alvin Chen, Cambridge, MA (US); Shyam Bharat, Arlington, MA (US); Ramon Quido Erkamp, Swampscott, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 650 days.

(21) Appl. No.: 17/634,752

(22) PCT Filed: Aug. 12, 2020

(86) PCT No.: PCT/EP2020/072612
§ 371 (c)(1),
(2) Date: Feb. 11, 2022

(87) PCT Pub. No.: WO2021/028467
PCT Pub. Date: Feb. 18, 2021

(65) Prior Publication Data
US 2022/0273263 A1  Sep. 1, 2022

Related U.S. Application Data (60) Provisional application No. 62/887,190, filed on Aug. 15, 2019.

(30) Foreign Application Priority Data

Oct. 14, 2019  (EP) .................................... 19202898

(51) Int. Cl.
*A61B 8/00*  (2006.01)

(52) U.S. Cl.
CPC .......... *A61B 8/4245* (2013.01); *A61B 8/4461* (2013.01); *A61B 8/4488* (2013.01); *A61B 8/483* (2013.01); *A61B 8/54* (2013.01)

(58) Field of Classification Search
CPC ... A61B 8/4245; A61B 8/4461; A61B 8/4488; A61B 8/483; A61B 8/54; A61B 8/0841;
(Continued)

(56) References Cited

U.S. PATENT DOCUMENTS

| | | | |
|---|---|---|---|
| 6,443,896 B1 | 9/2002 | Detmer | |
| 6,544,175 B1 * | 4/2003 | Newman | ........... A61B 8/00 600/443 |

(Continued)

FOREIGN PATENT DOCUMENTS

| | | |
|---|---|---|
| JP | 2005323669 A | 11/2005 |
| WO | 2004086082 A1 | 10/2004 |

(Continued)

OTHER PUBLICATIONS

International Search Report and Written Opinion of PCT/PE2020/072612, dated Oct. 23, 2020.

*Primary Examiner* — Adil Partap S Virk (57) ABSTRACT

A system for localizing a three-dimensional field of view of a beamforming ultrasound imaging probe based on a position indicator disposed within said field of view. The beamforming ultrasound imaging probe transmits and receives ultrasound signals within a three-dimensional field of view comprising a plurality of predetermined sub-volumes, each sub-volume being defined by a two dimensional array of beams. A controller causes the beamforming ultrasound imaging probe to scan the sub-volumes sequentially by transmitting and receiving ultrasound signals corresponding to each beam. A tracking system determines a position of the (Continued)

position indicator within the three-dimensional field of view; and determines a sub-volume in which the position indicator is located. The controller causes the beamforming ultrasound imaging probe to provide a localized field of view including the position of the position indicator by constraining the transmitting and receiving of ultrasound signals to a portion of the sub-volume in which the position indicator is located.

20 Claims, 4 Drawing Sheets (58) Field of Classification Search
CPC .......... A61B 6/032; A61B 6/037; A61B 8/02; A61B 8/12; G01S 15/899; G01S 15/8993; G01S 15/8925; G10K 11/346
See application file for complete search history.

(56) References Cited

U.S. PATENT DOCUMENTS

| | | | |
|---|---|---|---|
| 6,733,458 B1 | 5/2004 | Steins | |
| 7,270,634 B2 * | 9/2007 | Scampini | G01S 7/52085 600/447 |
| 2003/0120150 A1 | 6/2003 | Govari | |
| 2004/0073111 A1 * | 4/2004 | Poland | G06T 7/33 600/437 |
| 2004/0081340 A1 * | 4/2004 | Hashimoto | A61B 8/463 382/128 |
| 2004/0193042 A1 | 9/2004 | Scampini | |
| 2005/0228278 A1 * | 10/2005 | Chalana | G06T 7/0012 600/437 |
| 2005/0228280 A1 | 10/2005 | Ustuner | |
| 2005/0286748 A1 * | 12/2005 | Yang | G06T 15/08 382/128 |
| 2007/0276254 A1 * | 11/2007 | Yang | G06T 7/149 600/463 |
| 2009/0054776 A1 * | 2/2009 | Sasaki | A61B 8/483 600/443 |
| 2012/0069347 A1 | 3/2012 | Klein | |
| 2012/0123267 A1 * | 5/2012 | Dow | A61B 8/483 600/443 |
| 2012/0245465 A1 * | 9/2012 | Hansegard | A61B 8/466 600/443 |
| 2013/0072797 A1 * | 3/2013 | Lee | G01S 15/8993 600/443 |
| 2013/0096430 A1 | 4/2013 | Yoshiara | |
| 2013/0150718 A1 * | 6/2013 | Dixon | G01S 7/52061 600/443 |
| 2014/0013849 A1 | 1/2014 | Gerard | |
| 2014/0051988 A1 * | 2/2014 | Lautenschlager | A61B 6/12 600/424 |
| 2015/0272549 A1 | 10/2015 | Samset | |
| 2016/0045184 A1 * | 2/2016 | Courtney | A61B 8/4494 600/424 |
| 2016/0120499 A1 * | 5/2016 | Vignon | G01S 15/8997 600/424 |
| 2016/0367322 A1 | 12/2016 | Jain | |
| 2018/0279996 A1 * | 10/2018 | Cox | G06T 7/215 |
| 2019/0159752 A1 | 5/2019 | Bharat | |
| 2020/0229796 A1 * | 7/2020 | Yang | A61B 8/145 |

FOREIGN PATENT DOCUMENTS

| | | | | |
|---|---|---|---|---|
| WO | | 2006109219 A1 | 10/2006 | |
| WO | | 2015101949 A1 | 7/2015 | |
| WO | WO-2018108638 A1 * | | 6/2018 | ........... A61B 34/20 |

* cited by examiner

ULTRASOUND-BASED DEVICE LOCALIZATION

CROSS-REFERENCE TO PRIOR APPLICATIONS

This application is the U.S. National Phase application under 35 U.S.C. § 371 of International Application No. PCT/EP2020/072612, filed on Aug. 12, 2020, which claims the benefit of U.S. Provisional Patent Application Ser. No. 62/887,190, filed Aug. 15, 2019 and European Patent Application No. 19202898.3, filed on Oct. 14, 2019. These applications are hereby incorporated by reference herein.

FIELD OF THE INVENTION

The invention relates to a system for localizing a three-dimensional field of view of a beamforming ultrasound imaging probe. The invention finds application in the medical ultrasound imaging field in particular and may be used with a variety of ultrasound imaging probes. Its use with transthoracic "TTE" ultrasound imaging probes, intravascular "IVUS", as well as transesophageal "TEE", transnasal "TNE", intracardiac "ICE", and transrectal "TRUS", ultrasound imaging probes, is contemplated.

BACKGROUND OF THE INVENTION

Interventional devices such as medical needles, catheters and surgical tools are often difficult to visualize in an ultrasound image due to the specular nature of their reflectivity, particularly at unfavorable incidence angles.

In this respect, document US 2004/193042 A1 relates to a three dimensional ultrasonic diagnostic imaging system that is operated to guide or observe the operation of an invasive medical device in three dimensions. The appearance of the invasive device in the three dimensional ultrasonic image is enhanced to be more readily observable by a clinician. The enhancement is produced by transmitting a greater ultrasonic beam density in a subvolumetric region including the invasive device than in the surrounding portion of the volumetric region. The beam density may be uniformly high in the subvolumetric region and uniformly low in the surrounding region, or may taper from a relatively high beam density around the invasive device to a minimum beam density at distances removed from the invasive device.

Another document WO 2015/101949 A1 describes a system for tracking a position of an interventional tool respective an ultrasound image plane. A plurality of ultrasound transducers disposed on the tool are used to track a distance of the interventional tool from the ultrasound image plane based on ultrasound tracking signals transmitted between the tool and a probe that generates the ultrasound image plane.

In the system described in document WO 2015/101949 A1, the positon of the interventional tool may be inherently registered to the ultrasound image plane when the tracking signals are either provided by or sensed within the ultrasound image plane. However, in order to sense such signals, and thereby provide the desired tracking, at least one of the ultrasound transducers should be within, or at least close to, the ultrasound image plane. A user may therefore have to manually adjust the positioning of the ultrasound probe in order to provide the desired tracking by bringing one of the sensors closer to the image plane. Thereafter, the user manually coordinates movements of the sensor-bearing interventional tool, and the ultrasound probe in order to maintain the desired positioning of the sensor(s) respective the ultrasound image plane.

The tracking system described in document WO 2015/101949 A1 may also be used with a three dimensional ultrasound imaging system. Again, so long as at least one of the ultrasound transducers remains within the field of view of the imaging probe, the position of the ultrasound transducers respective the 3D field of view, may be determined. The larger, three-dimensional field of view has an increased likelihood of encompassing the ultrasound transducer, reducing the need to manually adjust the positioning of the ultrasound probe. However, the penalty for using three-dimensional imaging over planar imaging is typically a reduced frame rate and/or image quality. In order to alleviate this tradeoff, a user may therefore reduce the imaged three-dimensional field of view to encompass a smaller volume, for example to image only an organ of interest. This smaller field of view, however, requires more manual positioning of the probe in order to accurately follow the positon of the interventional tool.

WO 2004/086082 discloses a three dimensional ultrasonic diagnostic imaging system which guides or observes the operation of an invasive medical device in three dimensions. The invasive medical device is shown in a detailed ultrasonic image. Detailed detailed and wide fields of view may be displayed separately or overlapping in spatial alignment.

WO 2006/109219 discloses another an intervention guidance system in which the location of an interventional medical device is determined based on image processing from live, three-dimensional ultrasound images, This localization is used to steer an ultrasound beam so as to alter the imaging plane.

Thus, there remains a need for an improved system for tracking a position of an interventional tool with a desired field of view whilst alleviating the above constraints.

SUMMARY OF THE INVENTION

In seeking to provide improved tracking, a system is provided for localizing a three-dimensional field of view of a beamforming ultrasound imaging probe based on a position indicator disposed within said field of view. A corresponding method and computer program product are also provided.

The invention is defined by the claims.

In accordance with some aspects of this disclosure the system includes a beamforming ultrasound imaging probe, a controller, and a tracking system. The tracking system may for example be an electromagnetic or optical or ultrasound tracking system. The beamforming ultrasound imaging probe transmits and receives ultrasound signals within a three-dimensional field of view comprising a plurality of predetermined sub-volumes, each sub-volume being defined by a two-dimensional array of beams. The controller causes the beamforming ultrasound imaging probe to scan the sub-volumes sequentially by transmitting and receiving ultrasound signals corresponding to each beam. The tracking system determines a position of the position indicator within the three-dimensional field of view and determines a sub-volume in which the position indicator is located. The controller causes the beamforming ultrasound imaging probe to provide a localized field of view by constraining the transmitting and receiving of ultrasound signals to a portion of the sub-volume in which the position indicator is located.

Thus, a sub-volume in which the position indicator is located is determined automatically, and a localized field of view based thereupon, is provided. This alleviates the need for a user to manually adjust the positioning of the ultrasound imaging probe in order to find the position indicator. Moreover, by dividing the entire field of view into such sub-volumes and scanning the sub-volumes sequentially, the need to search the entire three-dimensional field of view in order to provide the localized field of view is typically avoided, and thus the localized field of view is provided quickly.

Thereafter, the localized field of view automatically tracks the position indicator, moving the localized field of view in response to relative movement between the ultrasound imaging probe and the position indicator. This alleviates the need for manual adjustments of the ultrasound imaging probe to provide imaging in the vicinity of the position indicator.

If, for any reason, the position indicator is subsequently lost from the localized field of view; for example if a sudden movement of the ultrasound imaging probe moves the position indicator outside the localized field of view faster than its position can be tracked, the sequential scanning of the sub-volumes may be repeated to again determine a sub-volume in which the position indicator is located and thus provide a new localized field of view.

In accordance with one specific aspect of this disclosure, the system includes a beamforming ultrasound imaging probe, a controller, and an ultrasound tracking system. Moreover, the position indicator is an ultrasound sensor, and localizing the three-dimensional field of view of the beamforming ultrasound imaging probe is based on ultrasound signals detected by the ultrasound sensor. The ultrasound tracking system is further configured to: receive synchronization signals from the beamforming ultrasound imaging probe, the synchronization signals corresponding to a time of emission of the transmitted ultrasound signals for each beam; and to receive electrical signals generated by the ultrasound sensor in response to the ultrasound signals transmitted by the beamforming ultrasound imaging probe; and to determine the position of the position indicator within the three-dimensional field of view based on the received synchronization signals from the beamforming ultrasound imaging probe and the received electrical signals generated by the ultrasound sensor; and to determine the sub-volume in which the ultrasound sensor is located, based on the synchronization signals and the first scanned sub-volume having a maximum intensity beam for which an intensity of the generated electrical signals exceeds a predetermined threshold and is the maximum for the respective sub-volume. The controller causes the beamforming ultrasound imaging probe to provide the localized field of view comprising the maximum intensity beam by constraining the transmitting and receiving of ultrasound signals to a portion of the sub-volume in which the ultrasound sensor is located. This specific aspect of the disclosure shares the benefits described above. Advantageously since the tracking system uses the ultrasound signals, the spatial reference frame of the tracking system is inherently co-registered to the spatial reference frame of the imaging probe. By avoiding the need for a separate registration, more accurate tracking may be provided.

Other aspects of the disclosure are described with reference to the appended claims and drawings.

DETAILED DESCRIPTION OF THE INVENTION

Figure 1:
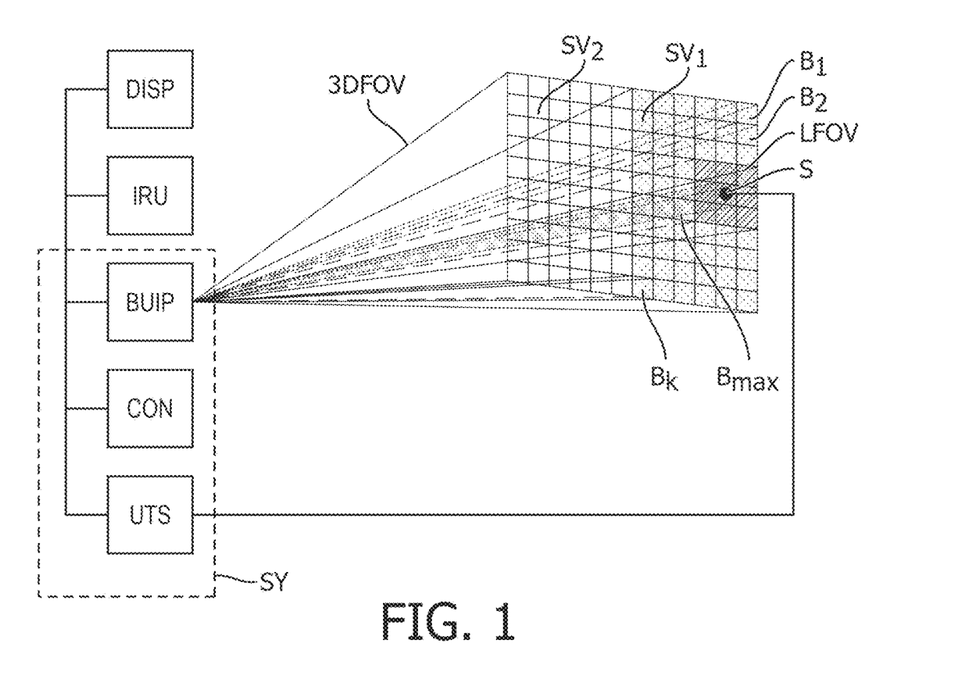
FIG. 1 illustrates a system SY including a beamforming ultrasound imaging probe BUIP with a three-dimensional field of view 3DFOV that includes sub-volumes $SV_{1\ldots n}$, each being defined by beams $B_{1\ldots k}$.

In order to illustrate the principles of the present invention, a system is described in which the three-dimensional field of view of a beamforming ultrasound imaging probe is localized based on a position indicator disposed within its field of view. The system includes a beamforming ultrasound imaging probe, a controller and a tracking system. Thereto, FIG. 1 illustrates a system SY including a beamforming ultrasound imaging probe BUIP with a three-dimensional field of view 3DFOV that includes sub-volumes $SV_{1\ldots n}$, each being defined by beams $B_{1\ldots k}$. Thus, three-dimensional field of view 3DFOV is divided into multiple sub-volumes $SV_{1\ldots n}$. As illustrated, each of sub-volumes $SV_{1\ldots n}$ includes multiple beams, exemplified by beams $B_{1\ldots k}$. Beams $B_{1\ldots k}$ may correspond to image lines in a three-dimensional ultrasound image and are generated using known beamforming techniques from the ultrasound field. These include controlling the relative delays between ultrasound signals transmitted by and received from individual transducers of a two-dimensional ultrasound transducer array of beamforming ultrasound imaging probe BUIP. Sub-volumes $SV_{1\ldots n}$ may be defined by assigning each of beams $B_{1\ldots k}$ to one of sub-volumes $SV_{1\ldots n}$. Whilst only two sub-volumes are illustrated in FIG. 1, other numbers and shapes of sub-volumes are also contemplated.

System SY in FIG. 1 may be used to localize three-dimensional field of view 3DFOV of beamforming ultrasound imaging probe BUIP based on a position indicator S disposed within said field of view 3DFOV. As illustrated in FIG. 1, system SY may optionally also include image reconstruction unit IRU, which may generate a reconstructed ultrasound image based on ultrasound imaging signals from beamforming ultrasound imaging probe BUIP, and display DISP which may display the reconstructed ultrasound image. As described in more detail below, each of items UTS, CON, BUIP, IRU and DISP may include electronic circuitry and/or one or more processors together with one or more memories that store instructions which when executed by the processor(s) implement one or more method steps corresponding to their described functionality. The electronic circuitry, processor(s) and memory(/ies) may be shared between one or more of items UTS, CON, BUIP, IRU and DISP.

Beamforming ultrasound imaging probe BUIP in FIG. 1 may for example, and without limitation, be a transthoracic "TTE" ultrasound imaging probe, an intravascular "IVUS", a transesophageal "TEE", transnasal "TNE", intracardiac "ICE", or a transrectal "TRUS", ultrasound imaging probe.

FIG. 1 also illustrates position indicator S that is disposed within three-dimensional field of view 3DFOV. Position indicator S may be a passive device or an active device. Non-limiting examples of a passive device include an ultrasound reflector or a permanent magnet. Non-limiting examples of active devices include an ultrasound sensor or emitter, a magnetic sensor or magnetic field generator, an optical sensor or emitter. In some implementations the position indicator may be disposed on an interventional device. The interventional device, may for example, and without limitation, be a medical needle, a catheter, a guidewire, a probe, an endoscope, an electrode, a robot, a filter device, a balloon device, a stent, a mitral clip, a left atrial appendage closure device, an aortic valve, a pacemaker, an intravenous line, a drainage line, a surgical tool, a tissue sealing device, a tissue cutting device or an implantable device.

As illustrated, controller CON in FIG. 1 is in communication with the ultrasound tracking system UTS and beamforming ultrasound imaging probe BUIP. The functionality of controller CON in FIG. 1 may be provided electronic circuitry and/or one or more memories that store instructions and one or more processors that execute the instructions. When executed by the processor, the instructions cause system SY that includes controller CON to implement a process that includes causing beamforming ultrasound imaging probe BUIP to scan sub-volumes $SV_{1...n}$ sequentially by transmitting and receiving ultrasound signals corresponding to each beam $B_{1...k}$. For instance, when sub-volumes $SV_{1...n}$ are arranged in a one-dimensional array, linear scanning of the array of sub-volumes is contemplated. When sub-volumes $SV_{1...n}$ are arranged in a two-dimensional array, raster scanning of the array of sub-volumes is contemplated.

As illustrated, tracking system UTS in FIG. 1 is in communication with beamforming ultrasound imaging probe BUIP. The functionality of tracking system UTS in FIG. 1 may be provided electronic circuitry and/or one or more memories that store instructions and one or more processors that execute the instructions. When executed by the processor, the instructions cause system SY that includes ultrasound tracking system UTS to implement a process that includes determining a position of position indicator S within the three-dimensional field of view 3DFOV and determining a sub-volume $SV_{1...n}$ in which position indicator S is located. Various tracking systems may be used as tracking system UTS, including ultrasound, (electro) magnetic, and optical tracking systems such as those described respectively in documents WO 2015/101949 A1, US 2003/0120150 A1 and US 2012/0069347 A1. The position of position indicator S within three-dimensional field of view 3DFOV, may in some implementations be a beam, selected from beams $B_{1...k}$, in which position indicator S is located, or in other implementations a three-dimensional position of position indicator S respective beamforming ultrasound imaging probe BUIP. The three-dimensional positon may be represented in e.g. a cartesian or a polar coordinate system, or by the combination of a time or flight or range between position sensor S and beamforming ultrasound imaging probe BUIP and a beam, selected from beams $B_{1...k}$, in which position indicator S is located. In some implementations, determining the position of position indicator S within three dimensional field of view 3DFOV may include registering a coordinate frame of tracking system UTS to a coordinate frame to which beams $B_{1...k}$ are referenced. Such a registration may be used to determine the sub-volume $SV_{1...n}$ in which position indicator S is located. In other implementations, described later, the coordinate frame of tracking system UTS may be inherently registered to the to coordinate frame to which beams $B_{1...k}$ are referenced and thus no registration may be required.

Subsequently, controller CON implements a process that includes causing beamforming ultrasound imaging probe BUIP to provide a localized field of view LFOV including the position of position indicator S by constraining the transmitting and receiving of ultrasound signals to a portion of the sub-volume in which position indicator S is located. This is illustrated in FIG. 1 by means of the constraining of ultrasound signals to the hatched beams which comprise localized field of view LFOV, which are in this particular example surround and are centred on the beam $B_{max}$ in which position sensor S is located.

Thereafter, the localized field of view automatically tracks the position indicator, moving the localized field of view in response to relative movement between the ultrasound imaging probe and the position indicator. This alleviates the need for manual adjustments of the ultrasound imaging probe to provide imaging in the vicinity of the position indicator.

Constraining the transmitting and receiving of ultrasound signals to a portion of the sub-volume in which position indicator S is located may for example include constraining the transmitting and receiving of ultrasound signals to the entire sub-volume in which the sensor is located. Alternatively it may include constraining the transmitting and receiving of ultrasound signals to a predetermined selection of beams including the position or beam in which position indicator S is located, for example a two-dimensional plane that passes through said position or beam, or two or more two-dimensional intersecting planes that both intercept said position or beam, or providing a new beam pattern that includes the position or beam in which position indicator S is located. In some implementations the beamforming ultrasound imaging probe BUIP includes a transducer array and the three-dimensional field of view 3DFOV and the localized field of view LFOV may each have a depth of field, $DOF_{3DFOV}$, $DOF_{LFOV}$, along an axis passing through the transducer array TA. In these implementations the depth of field of the localized field of view $DOF_{LFOV}$ may be less than and within the depth of field of the three-dimensional field of view $DOF_{3DFOV}$.

In some implementations the three-dimensional field of view 3DFOV may have an angular extent in each of two orthogonal planes, and each sub-volume has an angular extent in one of the two orthogonal planes that is equal to the angular extent of the three-dimensional field of view in the corresponding plane.

In some implementations the three-dimensional field of view 3DFOV has an angular extent in each of two orthogonal planes, and each sub-volume $SV_{1...n}$ has an angular extent in both of the two orthogonal planes that is less than the angular extent of the three-dimensional field of view 3DFOV in the corresponding plane.

In some implementations controller CON may implement a process that includes recording the last position of position indicator S and if the position becomes lost or unreliable, for example a signal indicative of the position falls below a predetermined threshold, controller CON may implement a process that also includes scanning the plurality of sub-volumes $SV_{1 \ldots n}$ starting at the last sub-volume at which the position was known or reliable, for example the sub-volume in which the maximum intensity of the electrical signals exceeded the predetermined threshold. Adjacent sub-volumes to this sub-volume may be scanned subsequently. In other implementations, the sub-volumes may be scanned subsequently in a sequential, or in a random, or quasi-random manner.

As mentioned above, the use of various tracking systems in determining the position of position indicator S within three-dimensional field of view 3DFOV are contemplated. The tracking system may for example be an ultrasound, an (electro)magnetic, or an optical tracking system. The use of both active and passive tracking systems are contemplated, active tracking systems including an energy sensor or emitter as position indicator S, and passive tracking systems including a passive element such as a passive ultrasound reflector or fiducial or a magnet as position indicator S.

In one specific implementation described in particular detail below the tracking system is an ultrasound tracking system, position indicator S is an ultrasound sensor, and localizing the three-dimensional field of view 3DFOV of beamforming ultrasound imaging probe BUIP is based on ultrasound signals detected by the ultrasound sensor S. In an alternative ultrasound tracking system position indicator S is an ultrasound emitter, and localizing the three-dimensional field of view 3DFOV of beamforming ultrasound imaging probe BUIP is based on ultrasound tracking signals emitted by the ultrasound emitter S that are received by beamforming ultrasound imaging probe BUIP. The ultrasound tracking signals are processed by the beamforming ultrasound imaging probe BUIP and the ultrasound tracking system and a position of ultrasound emitter S within three-dimensional field of view 3DFOV is determined based on the time of flight of the tracking signals between ultrasound emitter S and beamforming ultrasound imaging probe BUIP and a beam selected from beams $B_{1 \ldots k}$ within which the tracking signals are received. Thus, the tracking signals are received and processed by beamforming ultrasound imaging probe as if they were an ultrasound echo received from within the three dimensional field of view 3DFOV. In yet another alternative ultrasound tracking system, a plurality of discrete ultrasound emitters or sensors are disposed on beamforming ultrasound imaging probe BUIP and triangulation is performed on the times of flight of ultrasound tracking signals respectively received by or emitted by an ultrasound sensor or emitter disposed within three dimensional field of view 3DFOV in order to determine a position of the ultrasound sensor or emitter disposed within three dimensional field of view 3DFOV.

When the tracking system is an ultrasound tracking system and position indicator S is an ultrasound sensor; ultrasound tracking system UTS may implement a process that includes receiving synchronization signals from beamforming ultrasound imaging probe BUIP, the synchronization signals corresponding to a time of emission of the transmitted ultrasound signals for each beam $B_{1 \ldots k}$; receiving electrical signals generated by ultrasound sensor S in response to the ultrasound signals transmitted by the beamforming ultrasound imaging probe BUIP; determining the position of the position indicator S within the three-dimensional field of view 3DFOV based on the received synchronization signals from the beamforming ultrasound imaging probe BUIP and the received electrical signals generated by the ultrasound sensor S; and determining the sub-volume $SV_{1 \ldots n}$ in which ultrasound sensor S is located, based on the synchronization signals and the first scanned sub-volume having a maximum intensity beam $B_{max}$ for which an intensity of the generated electrical signals exceeds a predetermined threshold and is the maximum for the respective sub-volume.

Thus, the synchronization signals identify the beam transmitted by beamforming ultrasound imaging probe BUIP, and by recording the corresponding intensity of each electrical signal generated by ultrasound sensor S, the beam $B_{max}$ that is closest to the ultrasound sensor position may be determined. Generated electrical signals that are below a predetermined threshold may be ignored, since these could be noise signals that would otherwise erroneously identify the beam closest to which the sensor is located. A maximum intensity beam $B_{max}$ is ultimately identified, this being the beam for which an intensity of the generated electrical signals exceeds a predetermined threshold and is the maximum for the respective sub-volume. The maximum intensity beam $B_{max}$ may thus be considered to represent the closest beam to ultrasound sensor S.

Moreover, controller CON implements a process that includes causing beamforming ultrasound imaging probe BUIP to provide the localized field of view LFOV comprising the maximum intensity beam $B_{max}$ by constraining the transmitting and receiving of ultrasound signals to a portion of the sub-volume in which the ultrasound sensor S is located.

Thereafter, automatic adjustments of the localized field of view such that that it includes the maximum intensity beam ensure that the localized field moves in response to movements of the ultrasound imaging probe and the sensor. This alleviates the need to manually adjust the position of the ultrasound imaging probe in order to ensure that it remains within the localized field of view.

The above-described ultrasound tracking system in which the tracking system and the beamforming ultrasound imaging probe BUIP share the same coordinate frame advantageously alleviates the need to register their respective coordinate frames. This removes the need for calibration and may be considered to provide more accurate position determination.

Sensor S that is used in the ultrasound tracking system described above may be any sensor that is capable of detecting ultrasound signals. The use of piezoelectric and Capacitive Micromachined Ultrasound Transducers, i.e. CMUT, sensors is contemplated in particular. A variety of piezoelectric materials may be used, including both hard and soft piezoelectric materials. Polyvinylidene fluoride, otherwise known as PVDF whose mechanical properties and manufacturing processes lend themselves to attachment to curved surfaces such as medical needles may in particular be used. Alternative materials include a PVDF co-polymer such as polyvinylidene fluoride trifluoroethylene, a PVDF terpolymer such as P(VDF-TrFE-CTFE). Preferably the ultrasound transducer is wrapped around an axis of the interventional device in order to provide sensing around 360 degrees of rotation about the axis although this need not always be the case. Implementations that use an ultrasound emitter as position indicator S, may likewise employ various materials including piezoelectric materials, or employ a CMUT emitter.

In implementations using the above-described ultrasound tracking system, the constraining the transmitting and receiving of ultrasound signals to various portions of the sub-volume are contemplated.

Figure 2:
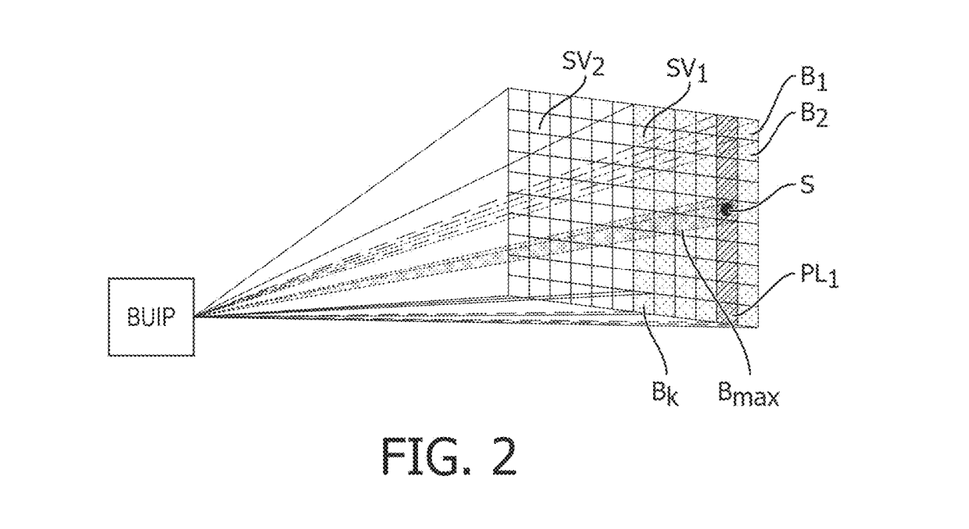
FIG. 2 illustrates a beamforming ultrasound imaging probe BUIP in which the transmitting and receiving of ultrasound signals is constrained to first two-dimensional plane $PL_1$ passing through maximum intensity beam $B_{max}$.

In some implementations that include an ultrasound tracking system and a position indicator S in the form of an ultrasound sensor the localized field of view LFOV may correspond to the entire sub-volume in which the sensor is located. In another implementations, as illustrated in FIG. 1, the portion of the sub-volume within which the transmitting and receiving of ultrasound signals is constrained may be a predetermined selection of beams surrounding the maximum intensity beam $B_{max}$. The predetermined selection of beams may be, but is not necessarily, centred on the maximum intensity beam $B_{max}$. In other implementations that include an ultrasound tracking system and a position indicator S in the form of an ultrasound sensor, and which are described with reference to FIG. 2, which illustrates a beamforming ultrasound imaging probe BUIP in which the transmitting and receiving of ultrasound signals is constrained to first two-dimensional plane $PL_1$ passing through maximum intensity beam $B_{max}$, the portion of the sub-volume within which the transmitting and receiving of ultrasound signals is constrained may be first two-dimensional plane $PL_1$ passing through the maximum intensity beam $B_{max}$. Various techniques for providing first two-dimensional plane $PL_1$ and other planes as defined herein are known from the ultrasound field. These may include controlling the various delays between ultrasound signals transmitted and received from a two-dimensional ultrasound transducer array within beamforming ultrasound imaging probe BUIP. Documents U.S. Pat. No. 6,443,896 B1 and US 2014/0013849 A1 describe exemplary techniques for providing and controlling such planes.

Figure 3:
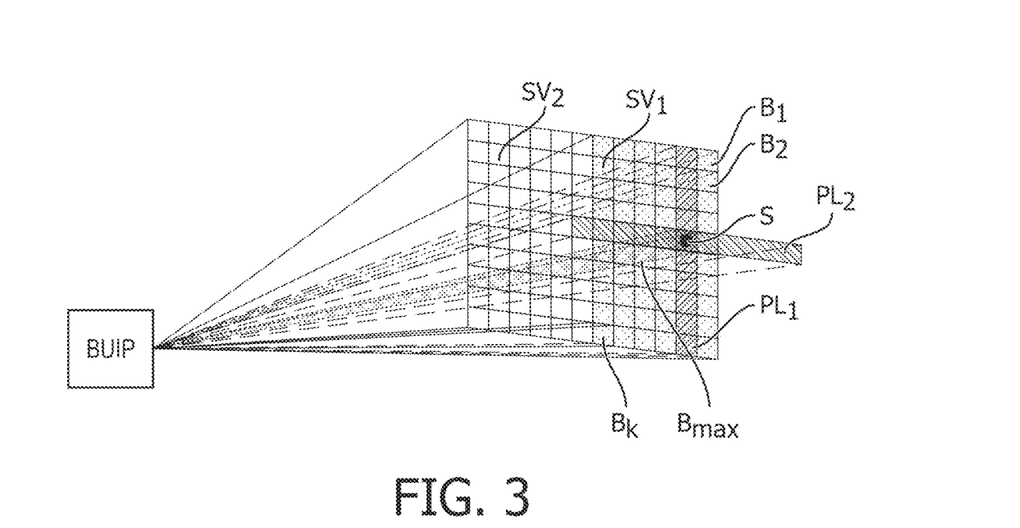
FIG. 3 illustrates a beamforming ultrasound imaging probe BUIP in which the transmitting and receiving of ultrasound signals is constrained to first two-dimensional plane $PL_1$ and in which beamforming ultrasound imaging probe BUIP also provides a second field of view corresponding to second two-dimensional plane $PL_2$.

In another implementation that include an ultrasound tracking system and a position indicator S in the form of an ultrasound sensor, a second two-dimensional plane $PL_2$ may additionally be provided. This is illustrated with reference to FIG. 3, which illustrates a beamforming ultrasound imaging probe BUIP in which the transmitting and receiving of ultrasound signals is constrained to first two-dimensional plane $PL_1$ and in which beamforming ultrasound imaging probe BUIP also provides a second field of view corresponding to second two-dimensional plane $PL_2$. With reference to FIG. 3, controller CON may further implement a process that includes causing beamforming ultrasound imaging probe BUIP to provide a second field of view by further transmitting and receiving ultrasound signals corresponding to a second two-dimensional plane $PL_2$, wherein said second two-dimensional plane $PL_2$ includes the maximum intensity beam $B_{max}$ and is arranged transversely with respect to the first two-dimensional plane $PL_1$. Thus, maximum intensity beam $B_{max}$ may be common to both first two-dimensional plane $PL_1$ and second two-dimensional plane $PL_2$, and thereby define the intersection between these planes. Second two-dimensional plane $PL_2$ may, as with first plane $PL_1$, be provided and controlled in accordance with known techniques as disclosed in for example document US 2014/0013849 A1. As illustrated, second two-dimensional plane $PL_2$ may optionally extend beyond the sub-volume in which position indicator S is located. In some implementations second two-dimensional plane $PL_2$ may be arranged orthogonally with respect to first two-dimensional plane $PL_1$, although other orientations of second two-dimensional plane $PL_2$ respective first two-dimensional plane $PL_1$ are also contemplated.

Figure 4:
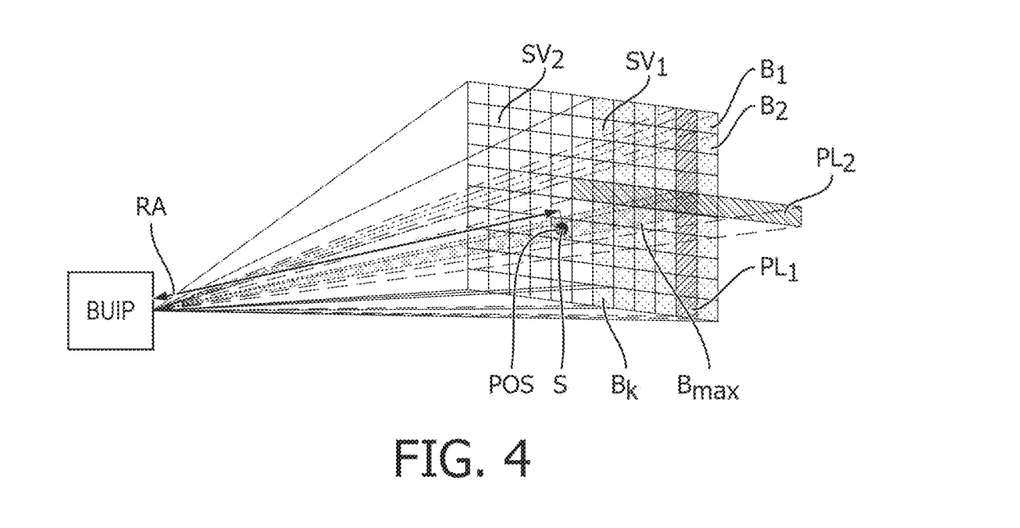
FIG. 4 illustrates a beamforming ultrasound imaging probe BUIP together with first two-dimensional plane $PL_1$ and second two-dimensional plane $PL_2$ and a three-dimensional location POS of position indicator S in the form of an ultrasound sensor.

FIG. 4 illustrates a beamforming ultrasound imaging probe BUIP together with first two-dimensional plane $PL_1$ and second two-dimensional plane $PL_2$ and a three-dimensional location POS of position indicator S in the form of an ultrasound sensor. With reference to FIG. 4, the beamforming ultrasound imaging probe BUIP of which may be implemented in place of beamforming ultrasound imaging probe BUIP in FIG. 1, ultrasound tracking system UTS may implement a process that further includes determining a three-dimensional location POS of sensor S respective beamforming ultrasound imaging probe BUIP. The three-dimensional location POS may be determined based on the maximum intensity beam $B_{max}$ and a range RA between beamforming ultrasound imaging probe BUIP and ultrasound sensor S for the maximum intensity beam $B_{max}$. The range RA may be computed from a time difference between a time of generation of the maximum generated electrical signal and a corresponding synchronization signal; the synchronization signal corresponding to a time of emission of the transmitted ultrasound signals for the maximum intensity beam $B_{max}$. Controller CON implements a process that includes causing beamforming ultrasound imaging probe BUIP to provide a second field of view by further transmitting and receiving ultrasound signals corresponding to a second two-dimensional plane $PL_2$, which passes through the three-dimensional location POS of the sensor S and is arranged transversely with respect to the first two-dimensional plane $PL_1$.

Figure 5:
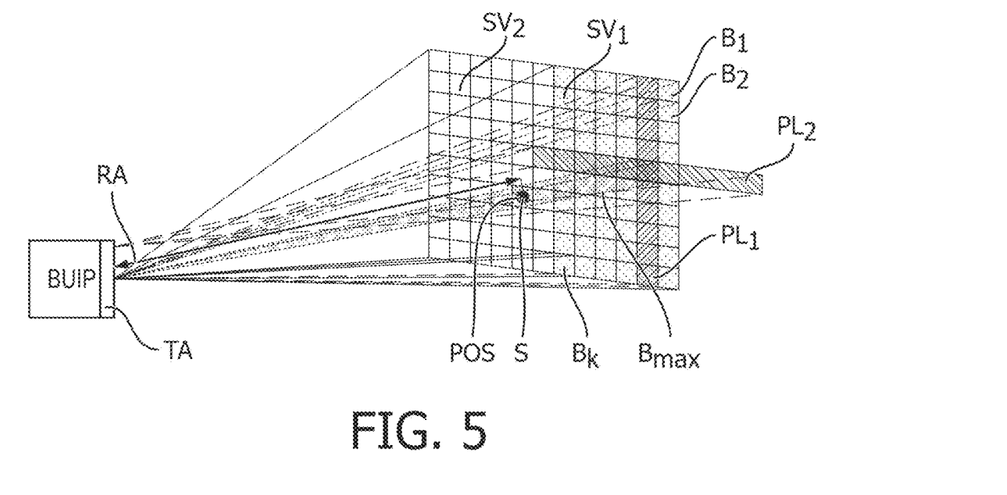
FIG. 5 illustrates another beamforming ultrasound imaging probe BUIP together with first two-dimensional plane $PL_1$ and second two-dimensional plane $PL_2$ and a three-dimensional location POS of position indicator S in the form of an ultrasound sensor.

FIG. 5 illustrates another beamforming ultrasound imaging probe BUIP together with first two-dimensional plane $PL_1$ and second two-dimensional plane $PL_2$ and a three-dimensional location POS of position indicator S in the form of an ultrasound sensor. Beamforming ultrasound imaging probe BUIP of FIG. 5 may be implemented in place of beamforming ultrasound imaging probe BUIP in FIG. 1. In contrast to FIG. 4, second two-dimensional plane $PL_2$ illustrated in FIG. 5 originates from a different position on transducer array TA of beamforming ultrasound imaging probe BUIP. As in FIG. 4, second two-dimensional plane $PL_2$ illustrated in FIG. 5 passes through three-dimensional location POS of sensor S.

Figure 6:
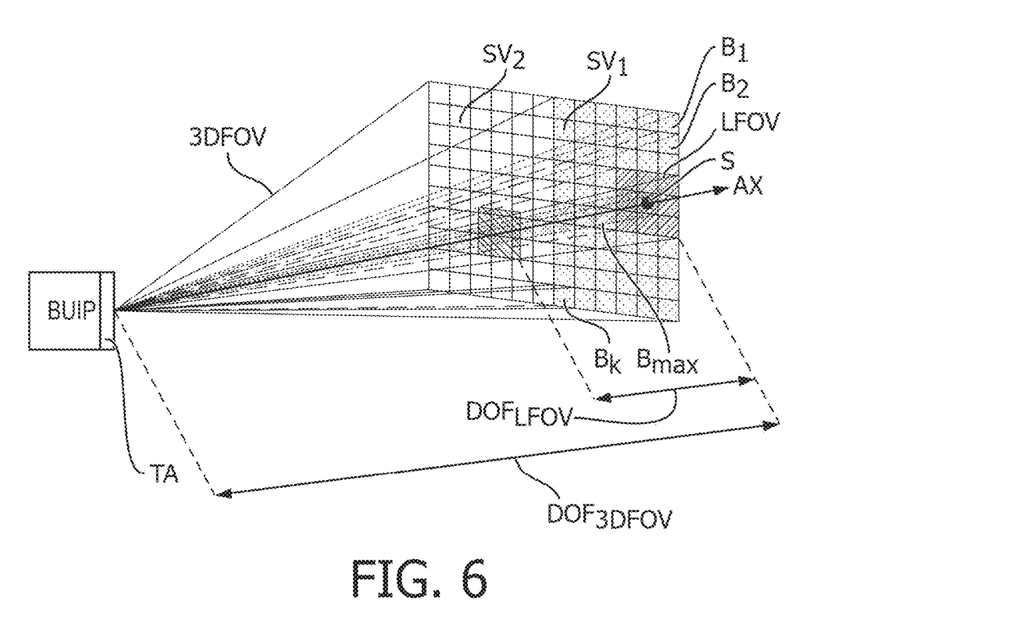
FIG. 6 illustrates a beamforming ultrasound imaging probe BUIP with three-dimensional field of view 3DFOV having depth of field $DOF_{3DFOV}$ and localized field of view LFOV having depth of field $DOF_{LFOV}$.

In some implementations that include an ultrasound tracking system and a position indicator S in the form of an ultrasound sensor, a depth of field of the localized field of view may be less than and within the depth of field of the three-dimensional field of view. An ultrasound image with the reduced depth of field may subsequently be displayed by display DISP in FIG. 1. Such a rendering may be termed "volume cropping" and is illustrated with reference to FIG. 6, which illustrates a beamforming ultrasound imaging probe BUIP with three-dimensional field of view 3DFOV having depth of field $DOF_{3DFOV}$ and localized field of view LFOV having depth of field $DOF_{LFOV}$. Beamforming ultrasound imaging probe BUIP of FIG. 6 may be implemented in place of beamforming ultrasound imaging probe BUIP in FIG. 1. In FIG. 6, beamforming ultrasound imaging probe BUIP includes transducer array TA, and the three-dimensional field of view 3DFOV and the localized field of view LFOV each have a depth of field $DOF_{3DFOV}$, $DOF_{LFOV}$ along an axis AX passing through the transducer array TA. The depth of field of the localized field of view $DOF_{LFOV}$ is less than and within the depth of field of the three-dimensional field of view $DOF_{3DFOV}$. Such a rendering allows for the removal of otherwise distracting information from the displayed ultrasound image.

In some implementations that include an ultrasound tracking system and a position indicator S in the form of an ultrasound sensor, the three-dimensional field of view 3DFOV may have an angular extent in each of two orthogonal planes, and each sub-volume may have an angular extent in one of the two orthogonal planes that is equal to the angular extent of the three-dimensional field of view in the corresponding plane.

In some implementations that include an ultrasound tracking system and a position indicator S in the form of an ultrasound sensor, the three-dimensional field of view 3DFOV has an angular extent in each of two orthogonal planes, and each sub-volume $SV_{1...n}$ has an angular extent in both of the two orthogonal planes that is less than the angular extent of the three-dimensional field of view 3DFOV in the corresponding plane.

In some implementations that include an ultrasound tracking system and a position indicator S in the form of an ultrasound sensor, controller CON may implement a process that includes recording the position of position indicator S, and if the position becomes lost or unreliable, for example the electrical signal corresponding to position POS falls below a predetermined threshold, controller CON may implement a process that also includes scanning the plurality of sub-volumes $SV_{1...n}$ starting at the last sub-volume at which the position was known or reliable, for example the sub-volume in which the maximum intensity of the electrical signals exceeded the predetermined threshold. Adjacent sub-volumes to this sub-volume may be scanned subsequently. In other implementations, the sub-volumes may be scanned subsequently in a sequential, or in a random, or quasi-random manner.

Figure 7:
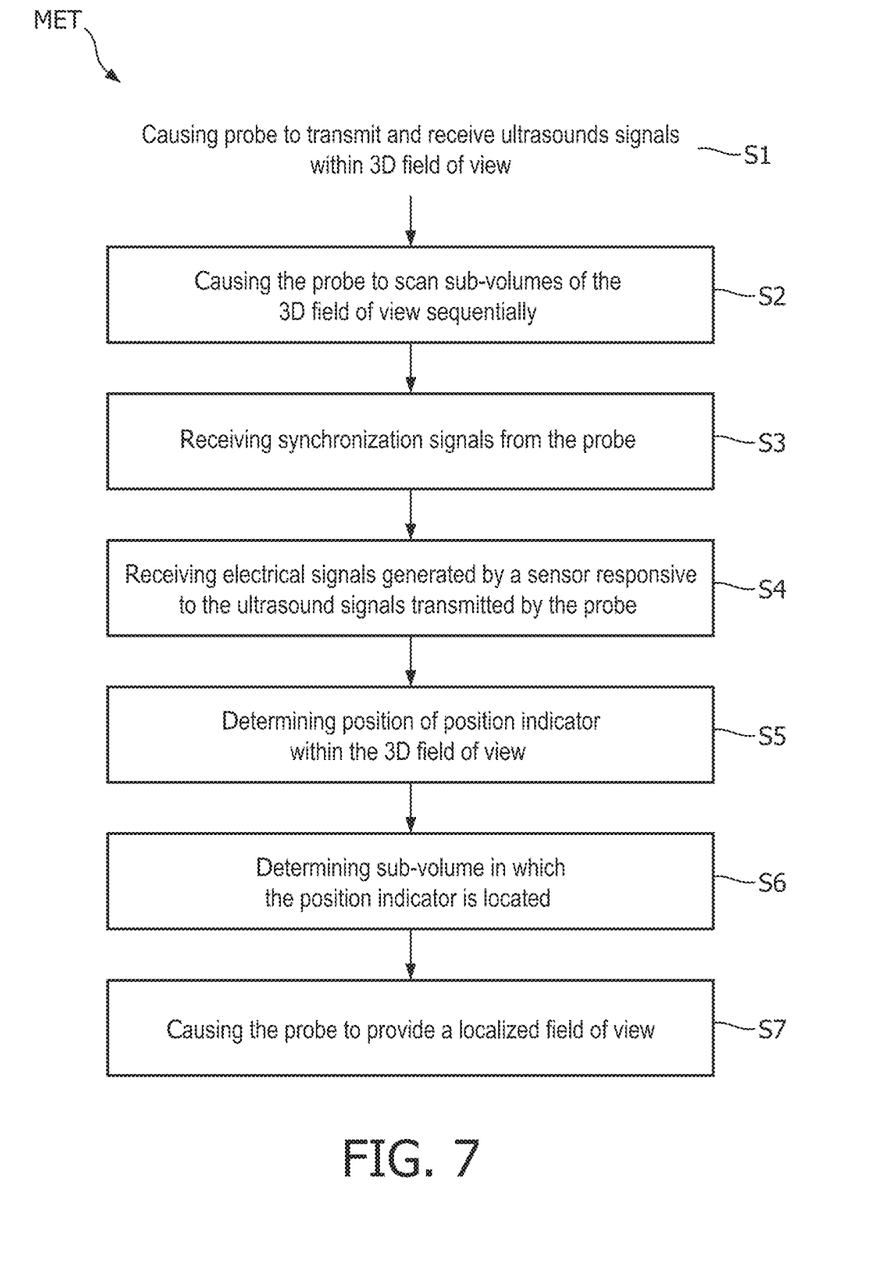
FIG. 7 illustrates a method MET that may be used in accordance with some aspects of the disclosure.

FIG. 7 illustrates a method MET that may be used in accordance with some aspects of the disclosure. It is noted that aspects disclosed in relation to the method or in relation to the system may be used interchangeably. Method MET may be used to localize a three-dimensional field of view 3DFOV of a beamforming ultrasound imaging probe BUIP based on a position indicator S disposed within the three-dimensional field of view 3DFOV. With reference to FIG. 7, in one implementation method MET may include the steps of:

causing S1 beamforming ultrasound imaging probe BUIP to transmit and receive ultrasound signals within three-dimensional field of view 3DFOV comprising a plurality of predetermined sub-volumes $SV_{1...n}$, each sub-volume $SV_{1...n}$ being defined by a plurality of beams $B_{1...k}$;

causing S2 beamforming ultrasound imaging probe BUIP to scan the sub-volumes $SV_{1...n}$ sequentially by transmitting and receiving ultrasound signals corresponding to each beam $B_{1...k}$;

determining S5 a position of the position indicator (S) within three-dimensional field of view 3DFOV;

determining S6 a sub-volume $SV_{1...n}$ in which position indicator S is located; and causing S7 beamforming ultrasound imaging probe BUIP to provide a localized field of view LFOV by constraining the transmitting and receiving of ultrasound signals to a portion of the sub-volume in which position indicator S is located.

In accordance with one specific implementation of method MET, and in which position indicator S is an ultrasound sensor; and in which localizing the three-dimensional field of view 3DFOV of the beamforming ultrasound imaging probe BUIP is based on ultrasound signals detected by the ultrasound sensor; method MET may further include the steps of:

receiving S3 synchronization signals from the beamforming ultrasound imaging probe BUIP, the synchronization signals corresponding to a time of emission of the transmitted ultrasound signals for each beam $B_{1...k}$; and receiving S4 electrical signals generated by the ultrasound sensor S in response to the ultrasound signals transmitted by the beamforming ultrasound imaging probe BUIP;

and wherein determining S5 the position of the position indicator S within three-dimensional field of view 3DFOV is based on the received synchronization signals from the beamforming ultrasound imaging probe BUIP and the received electrical signals generated by the ultrasound sensor S; and wherein the step of determining S6 the sub-volume SV1 . . . n in which the position indicator S is located is based on the synchronization signals and the first scanned sub-volume having a maximum intensity beam Bmax for which an intensity of the generated electrical signals exceeds a predetermined threshold and is the maximum for the respective sub-volume; and wherein the step of causing S7 the beamforming ultrasound imaging probe BUIP to provide the localized field of view LFOV further comprises providing the localized field of view LFOV comprising the maximum intensity beam Bmax.

One or more of the method steps disclosed herein, particularly those described in relation to the method of FIG. 7, may be recorded in the form of instructions which when executed on a processor cause the processor to carry out such method steps. The instructions may be stored on a computer program product. The computer program product may be provided by dedicated hardware as well as hardware capable of executing software in association with appropriate software. When provided by a processor, the functions can be provided by a single dedicated processor, by a single shared processor, or by a plurality of individual processors, some of which can be shared. Moreover, explicit use of the term "processor" or "controller" should not be construed to refer exclusively to hardware capable of executing software, and can implicitly include, without limitation, digital signal processor "DSP" hardware, read only memory "ROM" for storing software, random access memory "RAM", non-volatile storage, etc. Furthermore, embodiments of the present invention can take the form of a computer program product accessible from a computer-usable or computer-readable storage medium providing program code for use by or in connection with a computer or any instruction execution system. For the purposes of this description, a computer-usable or computer readable storage medium can be any apparatus that may include, store, communicate, propagate, or transport the program for use by or in connection with the instruction execution system, apparatus, or device. The medium can be an electronic, magnetic, optical, electromagnetic, infrared, or semiconductor system, or apparatus or device, or a propagation medium. Examples of a computer-readable medium include a semiconductor or solid state memory, magnetic tape, a removable computer diskette, a random access memory "RAM", a read-only memory "ROM", a rigid magnetic disk and an optical disk. Current examples of optical disks include compact disk-read only memory "CD-ROM", compact disk-read/write "CD-R/W", Blu-Ray™ and DVD.

In summary a system has been described for localizing a three-dimensional field of view of a beamforming ultrasound imaging probe based on a position indicator disposed within said field of view. The system includes a beamforming ultrasound imaging probe, a controller, and a tracking system. The beamforming ultrasound imaging probe transmits and receives ultrasound signals within a three-dimensional field of view comprising a plurality of predetermined sub-volumes, each sub-volume being defined by a plurality of beams. The controller causes the beamforming ultrasound imaging probe to scan the sub-volumes sequentially by transmitting and receiving ultrasound signals corresponding to each beam. The tracking system determines a position of the position indicator within the three-dimensional field of view; determines a sub-volume in which the position indicator is located; and the controller causes the beamforming ultrasound imaging probe to provide a localized field of view including the position of the position indicator by constraining the transmitting and receiving of ultrasound signals to a portion of the sub-volume in which the position indicator is located.

Various implementations and options have been described in relation to the system, and it is noted that these may be combined to achieve further advantageous effects. Any reference signs in the claims should not be construed as limiting the scope of the invention.

The invention claimed is:

1. A system for localizing a three-dimensional field of view, the system comprising:
   a beamforming ultrasound imaging probe is configured to transmit and receive ultrasound signals within the three-dimensional field of view comprising a plurality of predetermined sub-volumes, each sub-volume of the plurality of predetermined sub-volumes defined by a two-dimensional array of beams;
   a controller in communication with the beamforming ultrasound imaging probe, the controller comprising a first processor and is configured to cause the beamforming ultrasound imaging probe to scan the plurality of predetermined sub-volumes sequentially by transmitting and receiving ultrasound signals corresponding to each beam;
   a tracking system in communication with the beamforming ultrasound imaging probe and the controller, the tracking system comprising a second processor configured to:
      determine a position of a position indicator disposed within the three-dimensional field of view, and
      determine a sub-volume of the plurality of predetermined sub-volumes in which the position indicator is located based on the scan of the plurality of predetermined sub-volumes; and
   the first processor of the controller further configured to:
      cause the beamforming ultrasound imaging probe to scan the plurality of predetermined sub-volumes by transmitting and receiving ultrasound signals corresponding to each beam of the two-dimensional array of beams, and
      cause the beamforming ultrasound imaging probe to provide a localized field of view including the position of the position indicator by constraining the transmitting and receiving of ultrasound signals by the beamforming ultrasound imaging probe to a portion of the determined sub-volume in which the position indicator is located.

2. The system according to claim 1,
   wherein the position indicator is an ultrasound sensor;
   wherein the first processor of the controller is further configured to localize the three-dimensional field of view of the beamforming ultrasound imaging probe based on ultrasound signals detected by the ultrasound sensor;
   wherein the tracking system is an ultrasound tracking system; and
   wherein the second processor of the ultrasound tracking system is further configured to:
      receive synchronization signals from the beamforming ultrasound imaging probe, the synchronization signals corresponding to a time of emission of transmitted ultrasound signals for each beam of the two-dimensional array of beams, and
      receive electrical signals generated by the ultrasound sensor in response to ultrasound signals transmitted by the beamforming ultrasound imaging probe,
      determine the position of the position indicator within the three-dimensional field of view based on the received synchronization signals from the beamforming ultrasound imaging probe and the received electrical signals generated by the ultrasound sensor, and
      determine the sub-volume in which the ultrasound sensor is located, based on the received synchronization signals and a first scanned sub-volume of the plurality of predetermined sub-volumes having a maximum intensity beam for which an intensity of the generated electrical signals exceeds a predetermined threshold and is maximum for the respective sub-volume; and
   wherein the first processor of the controller is further configured to cause the beamforming ultrasound imaging probe to provide the localized field of view comprising the maximum intensity beam by constraining transmitting and receiving of ultrasound signals to the portion of the sub-volume in which the ultrasound sensor is located.

3. The system according to claim 2, wherein the portion of the sub-volume is a first two-dimensional plane passing through a maximum intensity beam of the two-dimensional array of beams.

4. The system according to claim 3, wherein the first processor of the controller is further configured to;
   cause the beamforming ultrasound imaging probe to provide a second field of view by further transmitting and receiving ultrasound signals corresponding to a second two-dimensional plane,
   wherein the second two-dimensional plane includes the maximum intensity beam and is arranged transversely with respect to the first two-dimensional plane.

5. The system according to claim 3, wherein the second processor of the ultrasound tracking system is further configured to;
   determine a three-dimensional location of the ultrasound sensor respective the beamforming ultrasound imaging probe, the three-dimensional location of the ultrasound sensor determined based on the maximum intensity beam and a range between the beamforming ultrasound imaging probe and the ultrasound sensor for the maximum intensity beam, the range computed based on a time difference between a time of generation of a maximum generated electrical signal corresponding to the maximum intensity beam and a corresponding synchronization signal; and
   cause the beamforming ultrasound imaging probe to provide a second field of view by further transmitting and receiving ultrasound signals corresponding to a second two-dimensional plane, wherein the second two-dimensional plane passes through the three-dimensional location of the ultrasound sensor and is arranged transversely with respect to the first two-dimensional plane.

6. The system according to claim 2, wherein the portion of the sub-volume comprises a predetermined selection of beams surrounding the maximum intensity beam.

7. The system according to claim 6, wherein the predetermined selection of beams is centered on the maximum intensity beam.

8. The system according to claim 1,
wherein the beamforming ultrasound imaging probe comprises a transducer array, and wherein the three-dimensional field of view and the localized field of view each have a depth of field, along an axis passing through the transducer array; and
wherein the depth of field of the localized field of view is less than and within the depth of field of the three-dimensional field of view.

9. The system according to claim 1, wherein the three-dimensional field of view has an angular extent in each of two orthogonal planes, and wherein each sub-volume has an angular extent in one of the two orthogonal planes that is equal to the angular extent of the three-dimensional field of view in a corresponding orthogonal plane of the two orthogonal planes.

10. The system according to claim 1, wherein the three-dimensional field of view has an angular extent in each of two orthogonal planes, and wherein each sub-volume has an angular extent in both of the two orthogonal planes that is less than the angular extent of the three-dimensional field of view in a corresponding orthogonal plane of the two orthogonal planes.

11. The system according to claim 10, wherein the first processor of the controller is further configured to:
record a maximum intensity of electrical signals generated for the localized field of view; and
if the maximum intensity of the electrical signals generated for the localized field of view is below the predetermined threshold, scan the plurality of sub-volumes starting at a last sub-volume in which the maximum intensity of the electrical signals exceeded the predetermined threshold.

12. A method of localizing a three-dimensional field of view, the method comprising:
causing a beamforming ultrasound imaging probe to transmit and receive ultrasound signals within the three-dimensional field of view comprising a plurality of predetermined sub-volumes, each sub-volume of the plurality of predetermined sub-volumes being-defined by a two-dimensional array of beams;
causing the beamforming ultrasound imaging probe to scan the plurality of predetermined sub-volumes sequentially by transmitting and receiving ultrasound signals corresponding to each beam of the two-dimensional array of beams;
determining a position of a position indicator disposed within the three-dimensional field of view;
determining a sub-volume of the plurality of predetermined sub-volumes in which the position indicator is located based on the scanning of the plurality of predetermined sub-volumes; and
causing the beamforming ultrasound imaging probe to provide a localized field of view by constraining transmitting and receiving of ultrasound signals to a portion of the determined sub-volume in which the position indicator is located.

13. The method according to claim 12,
wherein the position indicator is an ultrasound sensor;
wherein localizing the three-dimensional field of view of the beamforming ultrasound imaging probe is based on ultrasound signals detected by the ultrasound sensor; and
wherein the method further comprises:
receiving synchronization signals from the beamforming ultrasound imaging probe, the synchronization signals corresponding to a time of emission of the transmitted ultrasound signals for each beam;
receiving electrical signals generated by the ultrasound sensor in response to the ultrasound signals transmitted by the beamforming ultrasound imaging probe;
determining the position of the position indicator within the three-dimensional field of view based on the received synchronization signals from the beamforming ultrasound imaging probe and the received electrical signals generated by the ultrasound sensor;
determining the sub-volume in which the position indicator is located is based on the synchronization signals and the first scanned sub-volume having a maximum intensity beam for which an intensity of the generated electrical signals exceeds a predetermined threshold and is maximum for the respective sub-volume; and
causing the beamforming ultrasound imaging probe to provide the localized field of view to include the maximum intensity beam.

14. The method according to claim 12, further comprising:
causing the beamforming ultrasound imaging probe to provide a second field of view by further transmitting and receiving ultrasound signals corresponding to a second two-dimensional plane,
wherein the portion of the sub-volume is a first two-dimensional plane passing through a maximum intensity beam of the two-dimensional array of beams, and
wherein the second two-dimensional plane includes the maximum intensity beam and is arranged transversely with respect to the first two-dimensional plane.

15. The method according to claim 14, further comprising:
determining a three-dimensional location of the ultrasound sensor respective the beamforming ultrasound imaging probe, the three-dimensional location of the ultrasound sensor determined based on the maximum intensity beam and a range between the beamforming ultrasound imaging probe and the ultrasound sensor for the maximum intensity beam, the range computed based on a time difference between a time of generation of a maximum generated electrical signal corresponding to the maximum intensity beam and a corresponding synchronization signal; and
causing the beamforming ultrasound imaging probe to provide a second field of view by further transmitting and receiving ultrasound signals corresponding to a second two-dimensional plane, wherein the second two-dimensional plane passes through the three-dimensional location of the ultrasound sensor and is arranged transversely with respect to the first two-dimensional plane.

16. A non-transitory computer-readable storage medium having a computer program product comprising instructions which, when executed by a processor, cause the processor to:

cause a beamforming ultrasound imaging probe to transmit and receive ultrasound signals within a three-dimensional field of view comprising a plurality of predetermined sub-volumes, each sub-volume of the plurality of predetermined sub-volumes defined by a two-dimensional array of beams;
cause the beamforming ultrasound imaging probe to scan the plurality of predetermined sub-volumes sequentially by transmitting and receiving ultrasound signals corresponding to each beam of the two-dimensional array of beams;
determine a position of a position indicator disposed within the three-dimensional field of view;
determining a sub-volume of the plurality of predetermined sub-volumes in which the position indicator is located based on the scan of the plurality of predetermined sub-volumes; and
causing the beamforming ultrasound imaging probe to provide a localized field of view by constraining transmitting and receiving of ultrasound signals to a portion of the determined sub-volume in which the position indicator is located.

17. The non-transitory computer-readable storage medium according to claim 16,
wherein the position indicator is an ultrasound sensor;
wherein the tracking system is an ultrasound tracking system; and
wherein the instructions, when executed by the processor, further cause the processor to:
localize the three-dimensional field of view of the beamforming ultrasound imaging probe based on ultrasound signals detected by the ultrasound sensor;
receive synchronization signals from the beamforming ultrasound imaging probe, the synchronization signals corresponding to a time of emission of transmitted ultrasound signals for each beam of the two-dimensional array of beams;
receive electrical signals generated by the ultrasound sensor in response to ultrasound signals transmitted by the beamforming ultrasound imaging probe;
determine the position of the position indicator within the three-dimensional field of view based on the received synchronization signals from the beamforming ultrasound imaging probe and the received electrical signals generated by the ultrasound sensor;
determine the sub-volume in which the ultrasound sensor is located, based on the received synchronization signals and a first scanned sub-volume of the plurality of predetermined sub-volumes having a maximum intensity beam for which an intensity of the generated electrical signals exceeds a predetermined threshold and is maximum for the respective sub-volume; and
cause the beamforming ultrasound imaging probe to provide the localized field of view comprising the maximum intensity beam by constraining transmitting and receiving of ultrasound signals to the portion of the sub-volume in which the ultrasound sensor is located.

18. The non-transitory computer-readable storage medium according to claim 17,
wherein the instructions, when executed by the processor, further cause the processor to cause the beamforming ultrasound imaging probe to provide a second field of view by further transmitting and receiving ultrasound signals corresponding to a second two-dimensional plane,
wherein the portion of the sub-volume is a first two-dimensional plane passing through a maximum intensity beam of the two-dimensional array of beams, and
wherein the second two-dimensional plane includes the maximum intensity beam and is arranged transversely with respect to the first two-dimensional plane.

19. The non-transitory computer-readable storage medium according to claim 18, wherein the instructions, when executed by the processor, further cause the processor to:
determine a three-dimensional location of the ultrasound sensor respective the beamforming ultrasound imaging probe, the three-dimensional location of the ultrasound sensor determined based on the maximum intensity beam and a range between the beamforming ultrasound imaging probe and the ultrasound sensor for the maximum intensity beam, the range computed based on a time difference between a time of generation of a maximum generated electrical signal corresponding to the maximum intensity beam and a corresponding synchronization signal; and
cause the beamforming ultrasound imaging probe to provide a second field of view by further transmitting and receiving ultrasound signals corresponding to a second two-dimensional plane, wherein the second two-dimensional plane passes through the three-dimensional location of the ultrasound sensor and is arranged transversely with respect to the first two-dimensional plane.

20. The non-transitory computer-readable storage medium according to claim 16,
wherein the beamforming ultrasound imaging probe comprises a transducer array, and wherein the three-dimensional field of view and the localized field of view each have a depth of field, along an axis passing through the transducer array; and
wherein the depth of field of the localized field of view is less than and within the depth of field of the three-dimensional field of view.

* * * * *